(12) United States Patent
Novac et al.

(10) Patent No.: US 10,184,911 B2
(45) Date of Patent: Jan. 22, 2019

(54) METHOD FOR MANUFACTURING HUMIDITY SENSOR

(71) Applicant: EM MICROELECTRONIC-MARIN S.A., Marin (CH)

(72) Inventors: Pinchas Novac, Neuchatel (CH); Amrane Belkacem, Montbeliard (CH); Yves Dupraz, Valeyres-sous-Montagny (CH)

(73) Assignee: EM MICROELECTRONIC MARIN S.A., Marin (CH)

( * ) Notice: Subject to any disclaimer, the term of this patent is extended or adjusted under 35 U.S.C. 154(b) by 245 days.

(21) Appl. No.: 14/973,995

(22) Filed: Dec. 18, 2015

(65) Prior Publication Data
US 2016/0178552 A1 Jun. 23, 2016

(30) Foreign Application Priority Data

Dec. 23, 2014 (EP) ..................................... 14200095

(51) Int. Cl.
*G01N 27/22* (2006.01)
(52) U.S. Cl.
CPC ................. *G01N 27/223* (2013.01)
(58) Field of Classification Search
CPC .................................................. G01N 27/223
See application file for complete search history.

(56) References Cited

U.S. PATENT DOCUMENTS

| 5,840,255 A * | 11/1998 | Kappel | G01N 27/12 338/34 |
|---|---|---|---|
| 2007/0131020 A1 | 6/2007 | Itakura et al. | |
| 2014/0054800 A1* | 2/2014 | Gatterbauer | H01L 24/05 257/782 |
| 2014/0077314 A1* | 3/2014 | Humbert | G01N 27/227 257/414 |

FOREIGN PATENT DOCUMENTS

| EP | 2 420 826 A1 | 2/2012 |
| WO | 2007/036922 A1 | 4/2007 |
| WO | 2009/066992 A2 | 5/2009 |

OTHER PUBLICATIONS

Ghandhi, "VLSI Fabrication Principles", 1983, pp. 517-519.*
Lei Gu, et al., "A novel capacitive-type humidity sensor using CMOS fabrication technology", Sensors and Actuators B: Chemical: International Journal Devoted to Research and Development of Physical and Chemical Transducers, Elsevier S.A, CH, May 1, 2004, pp. 491-498, vol. 99, No. 2-3.
J. Laconte, et al., "High-sensitivity Capacitive Humidity Sensor Using 3-Layer Patterned Polyimide Sensing Film", Proceedings of IEEE Sensors 2003 (IEEE Cat. No. 03CH37498) IEEE Piscataway, NJ, USA; [IEEE International Conference on Sensors], IEEE, Oct. 22, 2003, pp. 372-377, vol. 1.
European Search Report for EP 14 20 0095 dated Jun. 3, 2015.

* cited by examiner

*Primary Examiner* — Peniel M Gumedzoe
(74) *Attorney, Agent, or Firm* — Sughrue Mion, PLLC

(57) ABSTRACT

The present invention relates to a humidity sensor comprising a silicon base plate on which at least a plurality of (Continued)

dielectric layers, each provided with a metallic zone, and a metallic layer are arranged, said metallic layer being etched in order to form two electrodes, each comprising one armature provided with a multitude of arms, these armatures being mounted so that the arms of each armature are interlaced in order to have arms placed opposite each other and separated by gaps.

16 Claims, 4 Drawing Sheets

METHOD FOR MANUFACTURING HUMIDITY SENSOR

This application claims priority from European Patent Application No. 14200095.9 filed Dec. 23, 2014, the entire disclosure of which is hereby incorporated herein by reference.

The present invention relates to a humidity sensor comprising a silicon base plate on which at least a plurality of dielectric layers, each provided with a metallic zone, and a metallic layer are arranged, said metallic layer being etched in order to form two electrodes, each comprising one armature provided with a multitude of arms, these armatures being mounted so that the arms of each armature are interlaced in order to have arms placed opposite each other.

PRIOR ART

Humidity sensors for electronic circuits are known. Such a humidity sensor is a humidity sensor with interdigital combs.

Such a sensor is composed of a silicon wafer base on which at least one interlevel dielectric layer (ILD) is placed. On this interlevel layer, a plurality of intermetallic dielectric layers (IMD). These layers, preferably three in number, are superposed and each comprise metallic zones for electrical conduction.

Above these intermetallic dielectric layers, a conductive layer serving as interdigital comb is produced, this layer being able to be made of aluminium. This aluminium layer is then etched to form said comb. Once the comb is formed, the entirety is covered with a passivation layer.

This etched plate is next stored, then used during a second manufacturing phase during which it is prepared for use. This second manufacturing phase consists of an opening step during which the passivation layer is etched at the level of the comb and at the level of the contact areas. This step of etching the passivation makes it possible to etch the passivation layer situated between the various branches of the comb.

Once this step is finished, a protective layer for aluminium against corrosion is deposited, this layer being able to be a layer of oxynitride.

The last step consists of depositing a polyamide layer in order to protect the entirety.

However, this construction has disadvantages. A first disadvantage comes from the manufacture in two phases of said sensor. In fact, the fact of having two separate phases for manufacture of the sensor necessitates the presence of supplementary thermal cycles. These supplementary thermal cycles lead to the appearance of supplementary thermal stresses on the plate and the interdigital comb which can impair said humidity sensor.

A second disadvantage comes from the etching during the second phase. In fact, during the second phase during which the passivation layer is etched, parasitic capacitances appear. These parasitic capacitances are caused by the etching which is not perfect, i.e. the edges of which are not perfectly straight. Consequently, residues of the passivation layer are present leading to the appearance of these parasitic capacitances which impair performance.

SUMMARY OF THE INVENTION

To this end, the present invention consists of a humidity sensor comprising a silicon base sheet on which at least a plurality of dielectric layers, each provided with a metallic zone, and a metallic layer are arranged, said metallic layer being etched in order to form two electrodes, each comprising one armature provided with a multitude of arms, these armatures being mounted so that the arms of each armature are interlaced in order to have arms placed opposite each other and separated by gaps, characterised in that said sensor comprises furthermore a passivation layer (24) which is deposited on the etched metallic layer and in that said passivation layer is etched so that the gaps between the arms placed opposite each other are hollowed out, extending into the dielectric layer on which the metallic layer is deposited.

In a first advantageous embodiment, the sensor comprises furthermore an anticorrosion protective layer which protects the metallic layer from corrosion.

In a second advantageous embodiment, the anticorrosion protective layer is produced in oxynitride.

In a third advantageous embodiment, the protective layer produced in oxynitride has a thickness, the value of which is equal at most to 10% of the distance of the gaps between the arms placed opposite each other.

In a fourth advantageous embodiment, the sensor comprises furthermore a polyimide layer which serves as detection dielectric.

In a fifth advantageous embodiment, a passivation layer can be interposed deposited directly on the metallic layer at the level of the unproductive zones.

In another advantageous embodiment, the sensor is arranged to be integrated in a circuit system comprising a capacitance/voltage converter, an analogue-digital converter and a digital interface.

In another advantageous embodiment, the circuit system comprises furthermore contact areas which make it possible to connect it to a microcontroller.

The invention relates furthermore to a manufacturing method for a humidity sensor comprising the following steps:

1) providing a base plate;
2) depositing at least one dielectric layer, said dielectric layer being provided with a metallic zone and depositing a metallic layer on the last dielectric layer;
3) etching said metallic layer in order to form two electrodes, each comprising an armature provided with a multitude of arms, these armatures being mounted so that the arms of each armature are interlaced in order to have the arms placed opposite each other and separated by gaps;
4) depositing a passivation layer on said etched metallic layer;
5) etching said passivation layer at the level of the two electrodes, said etching being produced so as to extend, at the level of the gaps, between the arms placed opposite each other, into the dielectric layer on which the metallic layer is deposited.

In a first advantageous embodiment, the method comprises furthermore a step 6) consisting of depositing an anticorrosion protective layer which protects the metallic layer from corrosion.

In a second advantageous embodiment, the method comprises furthermore a step 7) consisting of etching said passivation layer at the level of at least one contact area which is etched during step 3).

In a third advantageous embodiment, the method comprises furthermore a step 8) consisting of depositing a polyimide layer on the last deposited layer.

In a fourth advantageous embodiment, the method comprises furthermore a step 9) consisting of etching said polyimide layer at the level of the contact areas in order to make it possible to arrange contact means.

In another advantageous embodiment, the method comprises furthermore a step 8a) consisting of arranging contact means.

In another advantageous embodiment, the method comprises furthermore a step 10) consisting of depositing a polyimide layer on the last deposited layer.

In another advantageous embodiment, the method comprises furthermore a step 5a) consisting of cleaning said sensor.

BRIEF DESCRIPTION OF THE FIGURES

The aims, advantages and features of the invention will appear more clearly in the following detailed description of at least one embodiment of the invention, given solely by way of example, in a non-limiting manner, and illustrated by the attached drawings in which.

DETAILED DESCRIPTION

Figure 1:
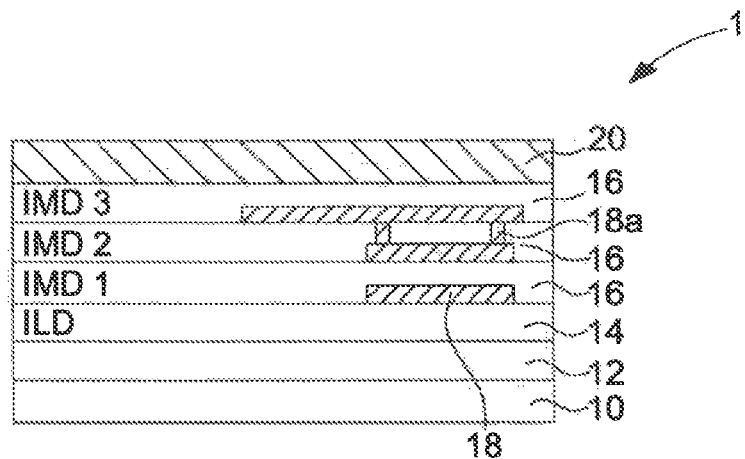
FIGS. 1 to 9 represent schematically the various steps for manufacturing a humidity sensor according to the invention.
Figure 10:
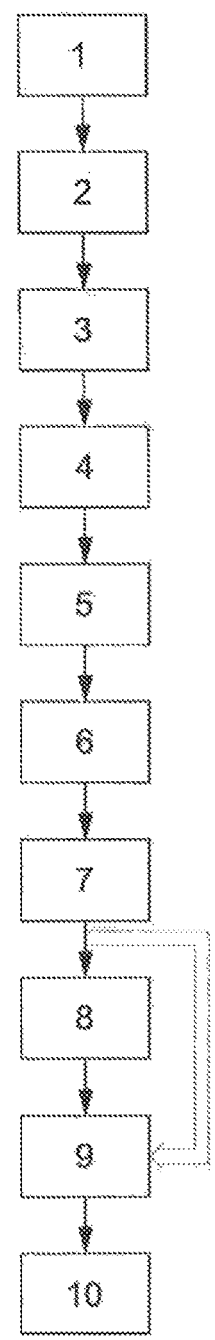
FIG. 10 represents a diagram of the steps of the method for manufacturing a humidity sensor according to the invention.

In FIG. 1, a humidity sensor 1 according to the invention is represented. Such a sensor comprises a silicon base plate 10 called wafer. This base plate can likewise comprise the circuit system in which the sensor will be integrated. This circuit system is composed of a capacitance/voltage converter, an analogue-digital converter and a digital interface, the entirety being able to be connected to a microcontroller arranged on another base plate via contact areas. Of course, it can be provided that the sensor, the circuit system and the microcontroller are on different base plates or on the same base plate or that the circuit system and the microcontroller are on the same plate. This base plate 10 serves as substrate for said sensor and a first step consists of providing this base plate. FIG. 10 represents various steps for manufacturing a humidity sensor according to the invention.

On this substrate 10, various layers are deposited successively during a second step. A first layer 12 is deposited. This layer comprises a zone termed active and a zone of silicon dioxide.

Over this first layer, an interlevel dielectric layer (ILD) 14 is deposited.

Subsequently, a plurality of intermetallic dielectric layers 16 (IMD) is deposited. These intermetallic dielectric layers 16, preferably three in number, are superposed and each comprise metallic zones 18 for the electrical conduction. These metallic zones 18 being able to be connected together by connectors of the VIA type 18a.

Above these intermetallic dielectric layers 16, a conductive layer 20 serving as interdigital comb is produced, this metallic layer 20 being deposited during the second step and can be made of aluminium as can be seen in FIG. 1. This second step is a step known to the person skilled in the art.

Figure 2:
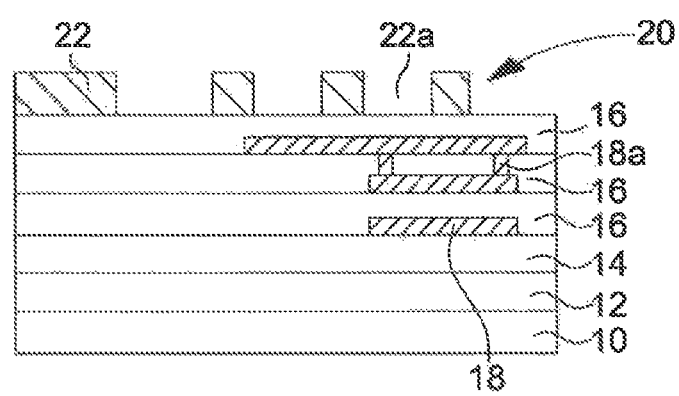

This aluminium layer 20 is etched during a third step in order to form said comb, as can be seen in FIG. 2. An interdigital comb is generally formed by two electrodes 22, each comprising an armature provided with a multitude of arms. These armatures are mounted so that the arms of each armature are interlaced. Thus a capacitive humidity sensor is obtained.

Figure 3:
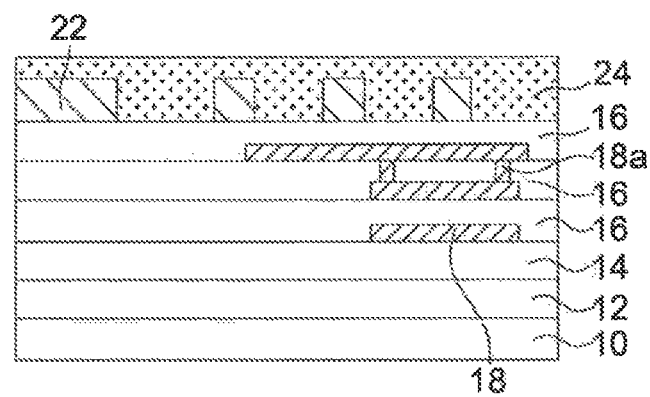

Once the comb is formed, a fourth step consists of covering the entirety with a passivation layer 24. This passivation layer 24 is used to protect the aluminium layer 20 against external attack, as can be seen in FIG. 3.

Once this passivation layer 24 is etched, an opening step or fifth step is achieved. Advantageously according to the invention, the opening step takes place during the same phase, i.e. in the continuity of the preceding steps. It is understood thus that the various steps making it possible to obtain the humidity sensor take place during a single procedural flow, i.e. the various steps of the manufacturing method are achieved one after the other without interrupting the conditions necessary for achieving these steps. This feature makes it possible therefore to reduce the cycle time.

Figure 4:
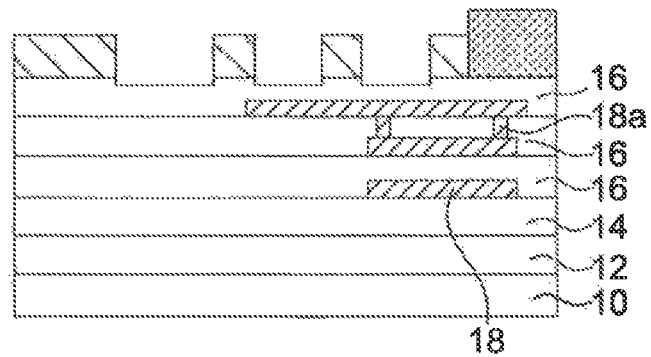
Figure 4:
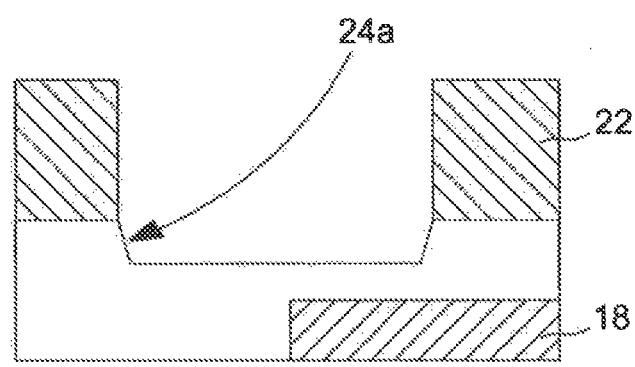

This opening step consists firstly in removing the passivation layer 24 at the level of the interdigital comb which forms the sensor 1 by etching. Once this passivation layer is removed, the invention expediently carries out the continuation of the etching. In fact, the passivation layer 24 is deposited on the comb, this layer 24 being deposited then in the gaps 22a between the various arms of the armatures forming the comb. When this passivation layer 24 is removed, this is not done entirely so that residues 24a remain at the level of the vertical walls of parts of the comb, as can be seen in FIG. 4'. These residues 24 between two arms of the comb, opposite each other, form a capacitor which has a capacitance, the formula of which is:

$$C = \varepsilon \times \frac{S}{d}$$

with S: surface of the opposite armatures, d: distance between the armatures and c the permittivity of the dielectric, this capacitance being in parallel with the detection capacitance and reduces the sensitivity of the humidity sensor.

This opening step is proposed to etch in the gaps 22a between the various parts of the armature of the comb. This etching is done expediently likewise to etch in the last intermetallic dielectric layer, the opening of the space between the metallic arms takes place by descending as far as the preceding metal, i.e. the metallic zone of the last intermetallic dielectric layer 16 with profiles of slices obtained quasi-vertical, without dielectric on the lateral walls of the capacitance and without residues via adequate cleaning, as can be seen in FIG. 4.

Thus, by hollowing out the dielectric layer 16, the distance between the two armatures of the capacitor is increased, each armature here having the shape of the residues of the passivation layer. Furthermore, by etching the dielectric layer 16 by more than the passivation layer, the size of the residues forming the armatures is reduced and consequently the surface is reduced, involving a reduction in the parasitic capacitance value. Thus a sensitivity of the humidity sensor 1 which is greater than the theoretical maximum published in the literature is obtained.

A fifth step can be carried out and consists of cleaning the surface in order to eliminate impurities which are present and due to the etching step.

Figure 5:
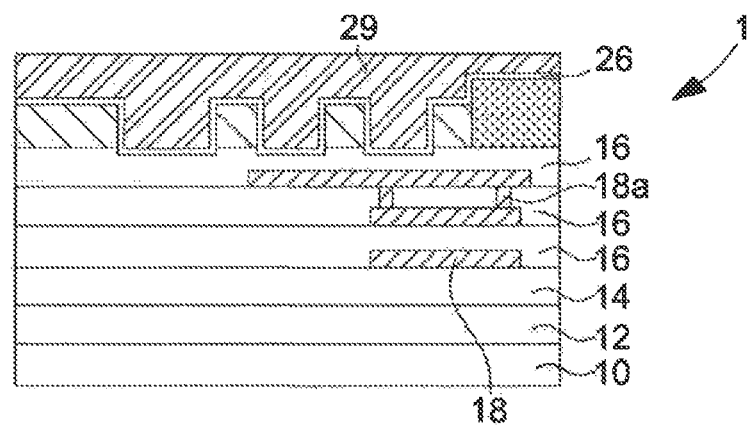

Once this fifth step is achieved, a sixth step consisting of depositing a protective layer 26 (capping layer or covering layer, humidity barrier, etc.) is carried out, as can be seen in FIG. 5. In fact, there is a risk of corrosion of the aluminium of the electrodes in contact with the polyimide which is a subsequently deposited protective layer, and diffusion of the aluminium into the polyimide. This protective layer makes it possible to prevent diffusion of the aluminium of the metallic layer 20 into the polyimide 29. In the case of our solution, this protective layer is produced in oxynitride (SiONx) with a thickness, the value of which is equal at most to 10% of the distance of the gaps between the arms placed opposite each other. In one example, if the distance is equal to 440 nm, the thickness will be from 20 nm±2 nm.

Figure 6:
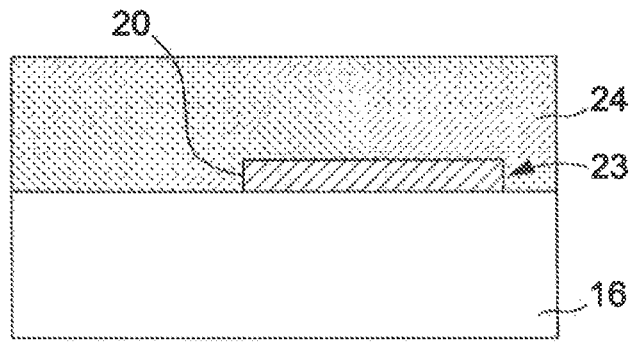
Figure 7:
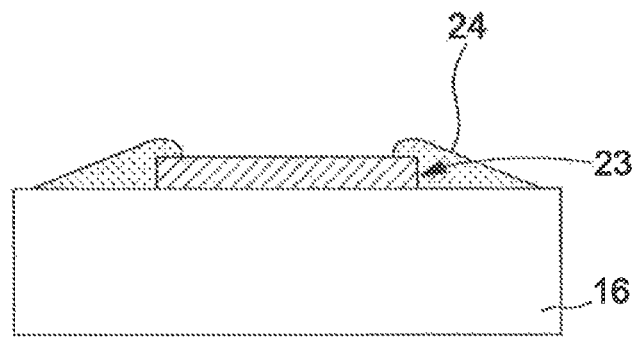

In a seventh step, the passivation layer 24 at the level of the contact areas 23 is open. These contact areas 23 are those of the circuit system in which the sensor is integrated. These areas are produced on a layer of metal deposited on an intermetallic dielectric. The contact areas thus released make it possible to place contact means there, as can be seen in FIGS. 6 and 7.

The contact means appear in two different forms and are produced during a step for putting the contacts in position.

According to a first form, the contact means are a connection wire using the method of wire or bridging cabling (also called wire bonding). In fact, the wire or bridging cabling is one of the techniques used to effect electrical connections between the casing and the integrated circuit. The cabling is produced simply by a wire (or bridge) welded between the two connection terminals provided for this use on each of the elements. The welding is generally produced by ultrasound. The material of the wire is aluminium, gold or copper. The diameter of the wire is of the order of 20 μm.

Figure 8:
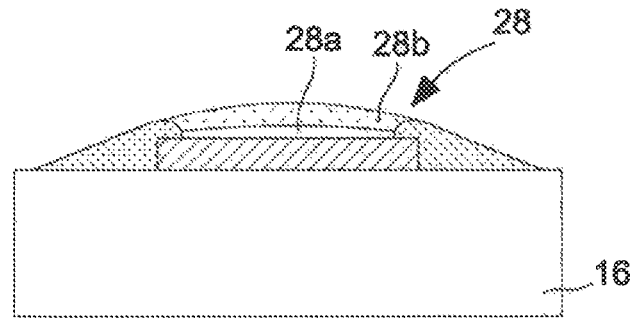
Figure 9:
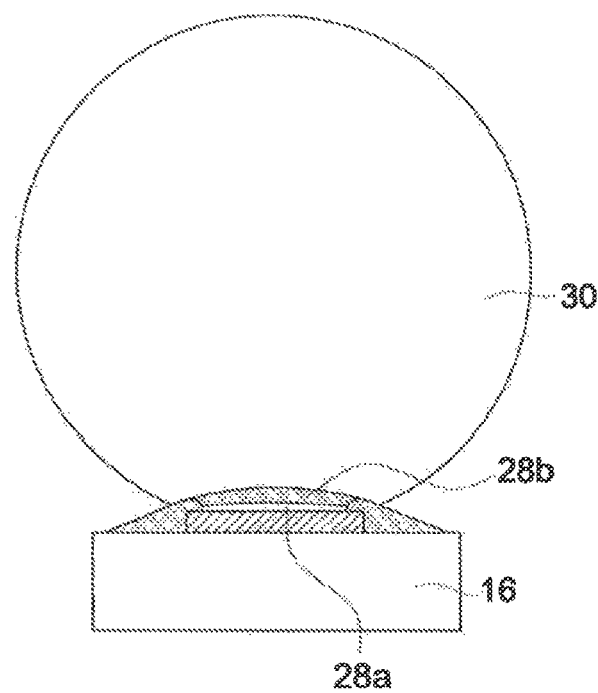

According to a second form which can be seen in FIGS. 8 and 9, the contact means have the shape of a ball. In fact, this ball connection technique (termed solder bumping) consists of depositing a tin ball 30 on the contact areas of the circuit, the latter being able to be produced in aluminium. In order to make this ball adhere, it is provided to have a fixing layer 28. Such a fixing layer is composed of a nickel layer 28a on which a gold layer 28b is placed, as can be seen in FIG. 8. The ball 30 is then placed on this fixing layer 28, as can be seen in FIG. 9.

A technique used for depositing the fixing layer is a technique termed electroless. This technique comprises a first step of cleaning the aluminium contact area in order to remove the oxides then removing the aluminium oxide in a second step. A third step consists of activating the aluminium with a layer of zinc, this zinc layer being removed during a fourth step. A fifth step is again a step for activating the aluminium contact area in order then to deposit a nickel layer. Finally a gold layer is deposited.

This technique advantageously uses chemical baths for the various steps so as not to subject the polyimide layer to temperature variations which are too great, risking impairing it and thus reducing the performance of the sensor. In fact, this electroless technique is used within the scope of the method according to the invention because it makes it possible to avoid fractures in the temperature conditions during the process of manufacturing the bumps. Given that the polyimide is sensitive to such rupture, it is necessary to use electrodes for this technique.

According to one embodiment, an eighth step is achieved after the opening step of the passivation layer 24 at the level of the contact areas. This eighth step consists of covering the assembly of the circuit with a polyimide layer 29, as can be seen in FIG. 5. This polyimide layer 29 is used as detection dielectric. In fact the polyimide is the layer which will react with the humidity in order to modify the dielectric constant in the gaps 22a between the arms placed opposite each other. This modification of the characteristics of the dielectric causes modification of the value of the capacitance. Following on this, the step for placing the contacts in position or ninth step is effected and consists of etching the polyimide 29 at the level of the contact areas in order then to deposit the fixing layer 28 and to position the ball or balls 30 which act as contact means.

According to another embodiment, the step of positioning the contacts, termed step 8a, is effected after the seventh step and consists of etching the passivation layer at the level of the contact areas in order then to deposit the fixing layer 28 and to position the ball or balls serving as contact means. After that, a step termed tenth step is achieved and consists of covering the circuit, apart from the contact areas, with a polyimide layer. This polyimide layer 29 can be deposited by a local deposition by jet method.

It will be understood that various modifications and/or improvements and/or combinations which are evident to the person skilled in the art can be applied to the various embodiments of the invention explained above without departing from the scope of the invention defined by the attached claims.

What is claimed is:

1. A method for manufacturing a humidity sensor comprising the following steps:
   1) providing a base plate;
   2) depositing at least one dielectric layer, said dielectric layer being provided with a metallic zone and depositing a metallic layer on a last dielectric layer;
   3) etching said metallic layer in order to form two electrodes, each comprising one armature provided with a multitude of arms, these armatures being mounted so that the arms of each armature are interlaced in order to have arms placed opposite each other and separated by gaps;
   4) depositing a passivation layer on said etched metallic layer;
   5) etching said passivation layer at a level of the two electrodes, said etching being produced so as to extend, at a level of the gaps, between the arms placed opposite each other, into the dielectric layer on which the metallic layer is deposited,
   wherein an underside of the two electrodes facing the dielectric layer on which the metallic layer is deposited is not exposed in said step 5).

2. The method according to claim 1, wherein it comprises furthermore a step 6) consisting of depositing an anticorrosion protective layer which protects the metallic layer from corrosion.

3. The method according to claim 1, wherein it comprises furthermore a step 7) consisting of etching said passivation layer at the level of at least one contact area which is etched during step 3).

4. The method according to claim 2, wherein it comprises furthermore a step 7) consisting of etching said passivation layer at the level of at least one contact area which is etched during step 3).

5. The method according to claim 3, wherein it comprises furthermore a step 8) consisting of depositing a polyimide layer on the last deposited layer.

6. The method according to claim 4, wherein it comprises furthermore a step 8) consisting of depositing a polyimide layer on the last deposited layer.

7. The method according to claim 5, wherein it comprises furthermore a step 9) consisting of etching said polyimide layer at the level of the contact areas in order to make it possible to arrange contact means.

8. The method according to claim 6, wherein it comprises furthermore a step 9) consisting of etching said polyimide layer at the level of the contact areas in order to make it possible to arrange contact means.

9. The method according to claim 3, wherein it comprises furthermore a step 8a) consisting of arranging contact means.

10. The method according to claim 4, wherein it comprises furthermore a step 8a) consisting of arranging contact means.

11. The method according to claim 9, wherein it comprises furthermore a step 10) consisting of depositing a polyimide layer on the last deposited layer.

12. The method according to claim 10, wherein it comprises furthermore a step 10) consisting of depositing a polyimide layer on the last deposited layer.

13. The method according to claim 1, wherein it comprises furthermore a step 5a) consisting of cleaning said sensor.

14. The method according to claim 9, wherein said step 8a) consisting of arranging the contact means uses a deposition technique for the fixing layer, termed electroless.

15. The method according to claim 10, wherein said step 8a) consisting of arranging the contact means uses a deposition technique for the fixing layer, termed electroless.

16. The method according to claim 6, wherein the anticorrosion protective layer is between the metallic layer and the polyimide layer.

* * * * *